United States Patent
Tsuchida et al.

(10) Patent No.: US 7,125,862 B2
(45) Date of Patent: Oct. 24, 2006

(54) PORPHYRIN-METAL COMPLEXES AND OXYGEN INFUSIONS CONTAINING THE SAME

(75) Inventors: Eishun Tsuchida, Tokyo (JP); Teruyuki Komatsu, Tokyo (JP); Yasuko Matsukawa, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 20 days.

(21) Appl. No.: 10/485,381

(22) PCT Filed: Jul. 30, 2002

(86) PCT No.: PCT/JP02/07734

§ 371 (c)(1),
(2), (4) Date: Apr. 19, 2004

(87) PCT Pub. No.: WO03/011866

PCT Pub. Date: Feb. 13, 2003

(65) Prior Publication Data

US 2004/0157820 A1  Aug. 12, 2004

(30) Foreign Application Priority Data

Jul. 30, 2001   (JP) .............................. 2001-229341

(51) Int. Cl.
- C07B 47/00 (2006.01)
- C07F 5/10 (2006.01)
- A61K 31/555 (2006.01)
- A61K 31/40 (2006.01)
- A61B 10/00 (2006.01)

(52) U.S. Cl. .................. 514/185; 514/9.1; 514/21; 514/410; 534/15; 540/145

(58) Field of Classification Search ............... 540/145; 534/15; 514/185, 410, 9.1, 21
See application file for complete search history.

(56) References Cited

U.S. PATENT DOCUMENTS 5,194,603 A * 3/1993 Tsuchida et al. ............ 540/145
5,773,417 A * 6/1998 Bonaventura ................ 514/21
6,008,198 A * 12/1999 Tsuchida et al. ............. 514/21

FOREIGN PATENT DOCUMENTS

JP  58-29787  2/1983
JP  6-271577  9/1994
WO  96/3426  2/1996

OTHER PUBLICATIONS

Teruyuki Komatsu et al, "Effect of Heme Structure on $O_2$-Binding Properties of Human Serum Albumin— Heme Hybrids: Intramolecular Histidine Cooridantion Provides a Stable $O_2$—Adduct Complex", Bioconjugate Chem., vol. 13, pp. 397-402, 2002.

Teruyuki Komatsu et al., "$O_2$-adduct complex of meso-tetrakis (α, α, α, α-o-pivalamidophenyl) porphinatoiron (II) with an intramolecularly coordinated proximal histidine," Chemistry Letters, No. 7, pp. 668 to 669, 2001.

* cited by examiner

*Primary Examiner*—James O. Wilson
*Assistant Examiner*—Paul V. Ward
(74) *Attorney, Agent, or Firm*—Wenderoth, Lind & Ponack, L.L.P.

(57) ABSTRACT

A porphyrin metal complex that can form a stable oxygen complex and acts effectively as an oxygen infusion, which comprises:

a transition metal ion M of period 4 or 5 coordinating to a porphyrin derivative represented by the following general

[I]

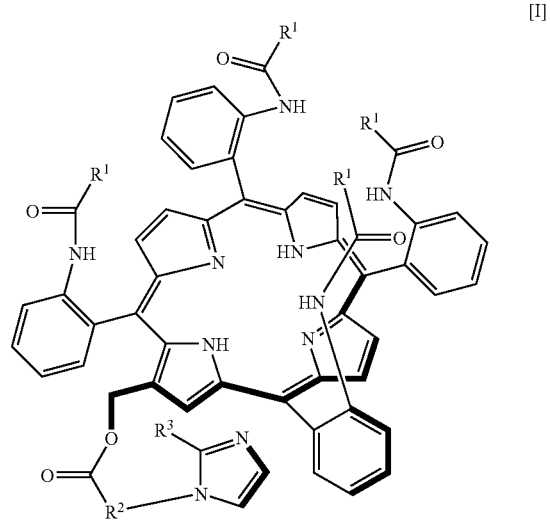

wherein $R^1$ is an alicyclic hydrocarbon group which may contain a substituent, $R^2$ is an alkylene group and $R^3$ is a group which does not hinder the coordination of an imidazolyl group to M.

34 Claims, No Drawings

PORPHYRIN-METAL COMPLEXES AND OXYGEN INFUSIONS CONTAINING THE SAME

TECHNICAL FIELD

The present invention relates to a novel porphyrin-metal complex that can bind and release oxygen reversibly, and to an oxygen infusion containing such porphyrin-metal complex, which can stably transport oxygen.

BACKGROUND ART

Hemes or porphinatoiron(II) complexes existing in hemoglobin and myoglobin play a role in the in vivo transport and storage of oxygen, and can reversibly bind and release molecular oxygen according to the partial pressure of oxygen. Since the 1970s, many reports have been made on studies to achieve oxygen adsorption-desorption functions similar to those of such natural hemes using synthetic porphinatoiron(II) complexes. Examples of early reports include J. P. Collman, *Acc. Chem. Res.*, 10, 265 (1977) and F. Basolo, B. M. Hoffman, J. A. Ibers, ibid, 8, 384 (1975). Particularly, 5,10,15,20-tetrakis($\alpha,\alpha,\alpha,\alpha$-o-pivalamidophenyl)porphinatoiron(II) complex (hereinafter referred to as "FeTpivPP complex") (J. P. Collman, et al., *J. Am. Chem. Soc.*, 97, 1427 (1975)) is known as a porphinatoiron(II) complex that can form a stable oxygen complex in ambient temperature conditions.

The FeTpivPP complex can reversibly bind and release molecular oxygen in ambient temperature in organic solvents such as benzene, toluene, dichloromethane, tetrahydrofuran or N,N-dimethylformamide, in the presence of an axial base such as 1-alkylimidazole and 1-alkyl-2-methylimidazole. Further, the same oxygen adsorption-desorption functions is seen even under physiological conditions (water-phase system, pH 7.4, $\leq 40°$ C.) by incorporating this complex into a bilayer membrane vesicle consisting of phospholipids (e.g., E. Tsuchida et al., *J. Chem. Soc., Dalton Trans.*, 1984, 1147 (1984)).

Here, the important point is that, firstly, as mentioned above, the addition of excess moles of the axial base molecule is required for the FeTpivPP complex to bind and release oxygen reversibly. However, certain imidazole derivatives that are widely used as axial base show pharmacological action, and often exhibit high internal toxicity. Also, when using phospholipid vesicles, the coexisting imidazole derivatives cause the morphology of the vesicles to become unstable. In order to reduce the amount of the axial base to a minimum, an imidazole derivative must be introduced into the molecule by covalent bonding.

The present inventors have considered that if, for example, an alkylimidazole derivative is covalently bonded as a substituent in the molecule of a porphinatoiron(II) complex, a stable oxygen carrier may be provided without external addition of an axial base, and have, so far, synthesized FeTpivPP analogues having substituents on the 2-position of the porphyrin ring, and observed reversible oxygen adsorption-desorption reaction for systems wherein such analogues were incorporated into phospholipid vesicles or human serum albumin (e.g., Japanese Patent Application Provisional Publication Nos. 59-164791, 59-162924 and 8-301873).

However, because the oxidation reaction of the central iron(II) is usually promoted in aqueous solutions than in organic solvents, the stability of the resulting oxygen complex is significantly low. In other words, reversible oxygen coordination activity is expressed only when the central iron of the porphyrin complex is in a divalent state; when the central iron is oxidized to form an iron(III) complex, the oxygen coordination activity is lost entirely (see, for example, Momentau et al., *Chem. Rev.*, 110, 7690 (1994)). The aforementioned prior art technologies developed by the present inventors, wherein the porphinatoiron(II) complex is dispersed in water, not only have the effect of uniformly dissolving the porphinatoiron(II) complex in water, but also of extending the stability of the oxygen complex by providing a hydrophobic space in the vicinity of oxygen coordination site. However, when considering the use of such aqueous solution and dispersions of porphinatoiron(II) complex as artificial oxygen carriers, for example as a substitute for red blood cells, designing and synthesis of a porphyrin molecular structure that is capable of forming a more stable oxygen complex was desired.

The invention of the present application has been developed in view of the above situations, and an object of the present invention is to solve the above-mentioned problems of the prior art and to provide a porphyrin metal complex that is effective as an oxygen infusion.

DISCLOSURE OF INVENTION

The present inventors have repeatedly and earnestly studied the molecular design and function expression for a porphyrin metal complex that can form a more stable oxygen complex; as a result, the inventors have found that by introducing an alicyclic hydrocarbon group as a substituent that is necessary to effectively provide oxygen-binding ability, in other words, as an oxygen coordination site-neighboring substituent, to the 2-position of 5,10,15,20-tetrakis($\alpha,\alpha,\alpha,\alpha$-o-substituted amidophenyl)porphyrin metal complex to which an imidazole derivative is bonded as a basic axial ligand, an oxygen infusion that is capable of forming oxygen complexes that are much higher in stability compared to those of formerly known systems, while maintaining oxygen affinity, may be obtained; thus, the present invention was completed.

Accordingly, the invention of the present application firstly provides a porphyrin metal complex comprising: a transition metal ion M of period 4 or 5 coordinating to a porphyrin derivative represented by the following general formula [I]

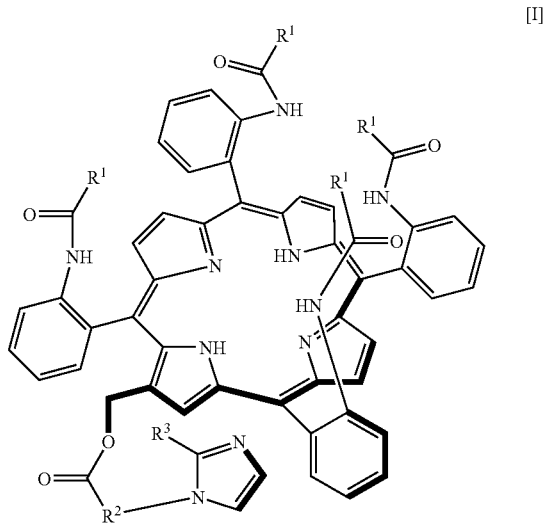

wherein $R^1$ is an alicyclic hydrocarbon group which may contain a substituent, $R^2$ is an alkylene group and $R^3$ is a group which does not hinder the coordination of an imidazolyl group to M.

The invention of the present application secondly provides a porphyrin metal complex represented by the following general formula [II]:

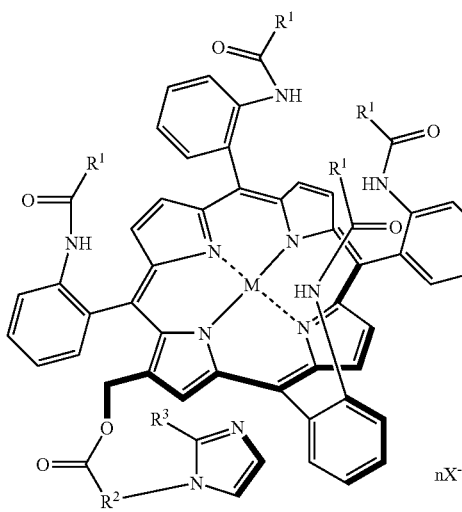

wherein M is a transition metal of period 4 or 5, $R^1$ is an alicyclic hydrocarbon group which may contain a substituent, $R^2$ is an alkylene group, $R^3$ is a group that does not hinder the coordination of the imidazolyl group to M, $X^-$ is a halogen ion and n denotes a number obtained by subtracting 2 from the valence number of M.

The invention of the present application provides, thirdly, the porphyrin metal complex of claims 1 or 2, wherein $R^1$ is an alicyclic hydrocarbon group that contains a substituent at the 1-position, fourthly, the porphyrin metal complex wherein $R^2$ is a $C_1$ to $C_{10}$ alkylene group and fifthly, the porphyrin metal complex wherein $R^3$ is a hydrogen atom or a substituent selected from the group consisting of a methyl group, an ethyl group and a propyl group.

The invention of the present application provides, sixthly, the porphyrin metal complex wherein M is Fe or Co, seventhly, the porphyrin metal complex wherein M is Fe(II) or Fe(III) and eighthly, the porphyrin metal complex wherein M is Co(II).

The invention of the present application provides, ninthly, an oxygen infusion containing at least any of the above porphyrin metal complexes, tenthly, an oxygen infusion prepared by incorporating and binding at least any one of the above porphyrin metal complexes in a phospholipid vesicle, a fatty oil microsphere, albumin or albumin multimer, and eleventhly, an oxygen infusion prepared by incorporating at least any one of the above porphyrin metal complexes into human serum albumin, recombinant human serum albumin, human serum albumin dimer or recombinant human serum albumin dimer.

BEST MODE FOR CARRYING OUT THE INVENTION

The porphyrin metal complex of the present invention comprises a transition metal ion M of period 4 or 5 coordinating to a porphyrin derivative represented by the following general formula [I]:

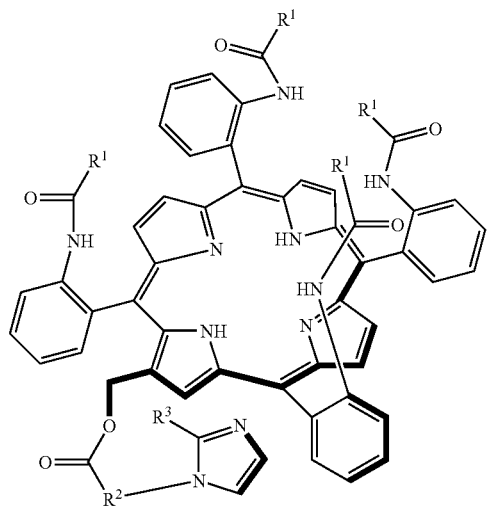

wherein $R^1$ is an alicyclic hydrocarbon group which may contain a substituent, $R^2$ is an alkylene group and $R^3$ is a group which does not hinder the coordination of an imidazolyl group to M. Specifically, the porphyrin metal complex is represented by the following general formula (II):

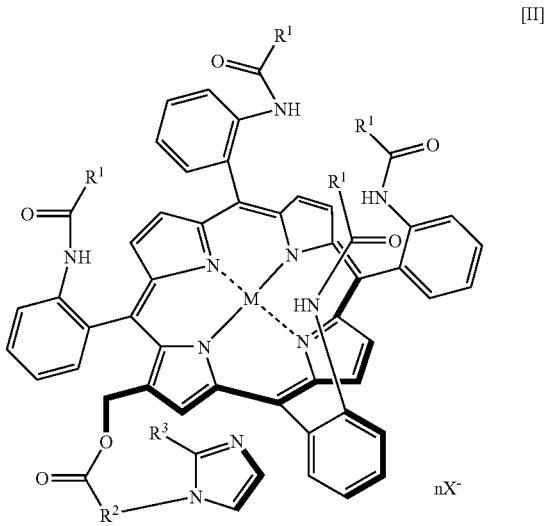

wherein M is a transition metal of period 4 or 5, $R^1$ is an alicyclic hydrocarbon group which may contain a substituent, $R^2$ is an alkylene group, $R^3$ is a group that does not hinder the coordination of the imidazolyl group to M, $X^-$ is a halogen ion and n denotes a number obtained by subtracting 2 from the valence number of M.

Here, when M in general formula [I] is a transition metal of period 4 or 5 such as Fe(II) and Co(II), this porphyrin metal complex is in a state where one imidazolyl group bound to the molecule is coordinated to M, and the compound can exhibit oxygen binding ability on its own.

Further, in the porphyrin metal complex of the present invention, because a more hydrophobic alicyclic hydrocarbon group is present as an oxygen coordination site-neighboring substituent, the oxidation process of the central metal by proton in water is more inhibited compared to the case of porphyrin derivatives containing t-butyl groups, which were previously reported by the present inventors. Consequently, an oxygen-coordinated complex of higher stability is obtained. Furthermore, because the substituent is a cyclic hydrocarbon group, such porphyrin metal complex has a characteristic that its molecular volume is suppressed to a level smaller than that of a long-chain alkyl group of the same carbon atoms. Such a small molecular volume is advantageous when incorporating the porphyrin metal complex into a microscopic hydrophobic environment such as the inside of albumin.

In the aforementioned porphyrin metal complex of the present invention, $R^1$, $R^2$ and $R^3$ are those as mentioned above and their type are not particular limited.

Preferable examples of $R^1$ include alicyclic hydrocarbons having a substituent at the 1-position such as 1-substituted cyclopropyl group, 1-substituted cyclopentyl group, 1-substituted cyclohexyl group, 1-methyl-2-cyclohexenyl group, 1-substiuted norbornyl group and 1-adamatyl group, which contain a substituent such as a methyl group, alkylamide group or alkyl ether at the 1-position. Of course, besides these examples, $R^1$ may be a 2-substituted norbornyl group.

In order to ensure that it does not inhibit the coordination of the imidazolyl group to M, $R^2$ is preferably an alkylene group of $C_1$ to $C_{10}$ so as not to increase the molecular volume too much.

$R^3$ may be any substituent as long as it does not inhibit the coordination of the imidazolyl group to M, and preferable examples include hydrogen atom, methyl group, ethyl group and propyl group.

Although any transition metal of period 4 or 5 may be used as the central transition metal M in the porphyrin metal complex of the present invention and is not particularly limited, Fe and Co give porphyrin metal complexes of high oxygen-binding/releasing abilities and are thus preferable. Among these transition metals, Fe(II) and Fe(III) are preferable when M is Fe and Co(II) is preferable when M is Co.

Since the aforementioned porphyrin metal complex of the invention of the present application exhibits reversible oxygen binding/releasing abilities, an oxygen infusion is obtained by using this porphyrin metal complex as an oxygen carrier. The composition of such oxygen infusion is not particularly limited as long as it contains the porphyrin metal complex of the present invention. Specific examples of the oxygen infusion include oxygen infusions prepared by incorporating the above porphyrin metal complex into a phospholipid vesicle, a fatty oil microsphere, albumin or albumin multimer, as well as oxygen infusions prepared by incorporating the above porphyrin metal complex into human serum albumin, recombinant human serum albumin, human serum albumin dimer or recombinant human serum albumin dimer. Of course, further to the porphyrin metal complex, the oxygen infusion may contain, water, a lipid, a phospholipid, a pH regulator, a stabilizer, a surfactant, a serum protein and the like in arbitrary proportions.

The oxygen infusions may be utilized as an analeptic for hemorrhagic shock, that is, as a substitute for blood infusion, as well as a preoperative blood diluent, a supplementary solution for extracorporeal circulation such artificial heart and lung, a perfusate for transplant organs, an oxygen supply solution for ischemic regions (e.g., myocardial infarction, cerebral infarction and respiratory insufficiency), a therapeutic agent for chronic anemia, a reflux agents for liquid ventilation, a sensitizers for cancer treatment or a culture solutions for regenerative tissue cells; furthermore, it may also be applied to patients of a rare blood type, patients refusing blood transfusion for religious reasons and animal care.

Moreover, the porphyrin complex having a transition metal ion of period 4 or 5 is highly useful as a catalysts for redox reaction, oxygen oxidation reaction and oxygen addition reaction, and thus, the porphyrin metal complex of the present invention may be utilized not only as the above-described oxygen infusion but also as a gas adsorbent, a redox catalyst, an oxygen oxidation reaction catalyst or an oxygen addition reaction catalyst.

Although the aforementioned porphyrin metal complex may be synthesized by any method, it may be synthesized, for example, by using 5,10,15,20-tetrakis(α,α,α,α-o-aminophenyl)porphyrin represented by the following general formula [III]

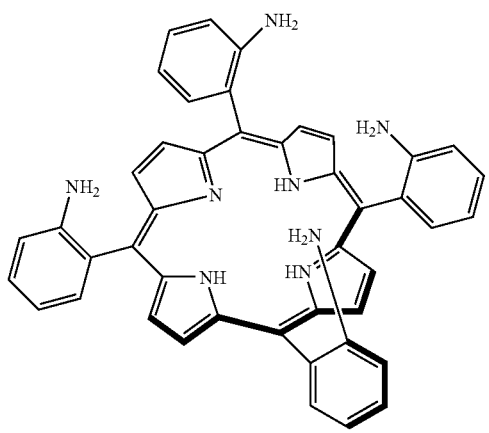

[III]

as a starting material.

In detail, 5,10,15,20-tetrakis(α,α,α,α-o-aminophenyl) porphyrin synthesized according to the method described in Collman et al., *J. Am, Chem. Soc.*, 97, 1427 (1975) is dissolved in an appropriate dry organic solvent, for example, dry tetrahydrofuran, after which a base (e.g., pyridine, triethylamine or 4-dimethylaminopyridine) and 1-methylcycloalkanic acid chloride are added and stirred in dark under ice-cooling or ambient temperature. Then, the solvents are removed under reduced pressure and the residue is extracted using an organic solvent such as chloroform, washed with water and subjected to filtration, followed by fraction-purification using silica gel chromatography. Thus, 5,10,15, 20-tetrakis(α,α,α,α-o-substituted amidophenyl)porphyrin is obtained.

Next, dimethylformamide that has been sufficiently deaerated is cooled using ice-water, to which phosphorous oxychloride is added and stirred at ambient temperature for 1 to 2 hours to prepare a Vilsmeier regent. 5,10,15,20-tetrakis (α,α,α,α-o-substituted amidophenyl)porphyrin dissolved in dry dichloromethane or chloroform is added dropwise to the reagent at ambient temperature. Here, the color of the reaction solution instantly changes from purple to green, which is the color of the dication. The reaction solution is refluxed for 12 to 24 hours. After cooling, an aqueous saturated sodium acetate solution is added to the reaction solution and the color of the reaction solution changes from green to purple, whereby the reaction solution is further stirred at 20 to 40° C. for 20 to 120 minutes. The reaction solution is extracted with an appropriate organic solvent, washed with water, dried and filtered, followed by fraction-purification using silica gel column chromatography. Thus, 2-formyl-5,10,15,20-tetrakis($\alpha,\alpha,\alpha,\alpha$-o-substituted amidophenyl)porphyrin is obtained.

This 2-formyl-5,10,15,20-tetrakis($\alpha,\alpha,\alpha,\alpha$-o-substituted amidophenyl)porphyrin is dissolved in an appropriate organic solvent (e.g., dichloromethane, chloroform or benzene), to which methanol is added, followed by sufficient deaeration using nitrogen. Sodium borohydride is added to the mixture under ice-cooling and the mixture is stirred for 5 to 15 minutes and water is added to the mixture to quench the reaction. The reaction solution is extracted with an organic solvent such as chloroform, the extract is washed with water, dried and filtered, followed by fraction-purification using silica gel column chromatography. Thus, 2-hydroxymethyl-5,10,15,20-tetrakis($\alpha,\alpha,\alpha,\alpha$-o-substituted amidophenyl)porphyrin is obtained.

The introduction of the imidazolylalkanoic acid to the 2-hydroxyethyl group of the 2-hydroxymethyl-5,10,15,20-tetrakis($\alpha,\alpha,\alpha,\alpha$-o-substituted amidophenyl)porphyrin thus obtained may be accomplished according to the method described in the prior art (JP-A No. 06-271577) developed by the present inventors.

Further, the introduction of a central metal into the resulting porphyrin derivative is achieved by a general method described in, for example, D. Dolphin (editor), The Porphyrin (1978), Academic Press, to obtain the corresponding porphyrin metal complex. Generally, a porphinatoiron (III) complex is obtained as an iron complex and a porphinatocobalt(II) complex is obtained as a cobalt complex.

It is to be noted that in the case where the porphyrin metal complex has the form of an iron(III) complex among the above porphyrin metal complexes, oxygen binding activity can be imparted by reducing the central metal to a divalent state from a trivalent state by conventional methods using an appropriate reducing agent (e.g., sodium dithionite, ascorbic acid, etc.).

In any of the systems wherein the porphinatoiron(II) complex is incorporated into: a bilayer membrane vesicle consisting of phospholipid molecules; a phospholipid coat fat emulsion; human serum albumin; recombinant human serum albumin; or albumin multimer, a stable oxygen complex is rapidly produced when it is in contact with oxygen. Further, these complexes can adsorb and desorb oxygen according to the partial pressure of oxygen. This oxygen-binding and releasing can be repeated reversibly and thus the porphinatoiron(II) complex acts as an oxygen adsorbent and as an oxygen carrier.

Gases other than oxygen that show metal coordinating abilities may form corresponding coordination complexes (e.g., carbon monoxide, nitrogen monoxide and nitrogen dioxide). Because of these reasons, the porphyrin metal complex of the present invention, particularly in the case of iron(II) or cobalt(II) complex, not only function as an effective oxygen infusion but may also be applied as a redox reaction catalyst in a homogenous or non-homogeneous system and as a gas adsorbent.

Hereinafter, the present invention will be described in further detail with reference to the following Examples. Of course, these examples are not intended to limit the present invention.

EXAMPLES

Example 1

0.4 g (0.59 mmol) of 5,10,15,20-tetrakis($\alpha,\alpha,\alpha,\alpha$-o-aminophenyl)porphyrin was dissolved in 55 ml of tetrahydrofuran followed by the addition of 1.7 ml (20.7 mmol) of pyridine and 2.11 g (14.8 mmol) of 1-methylcyclohexanic acid chloride, and stirred at ambient temperature in dark for 2 hours. Then, the solvents were removed under reduced pressure and the residue was extracted with chloroform. The extract was washed several times with aqueous 5% ammonia and with pure water. The chloroform layer was dried over sodium sulfate anhydride and subjected to filtration, followed by removal of solvents under reduced pressure. The residue was dissolved in a small amount of chloroform and subjected to fraction-purification by silica gel column (chloroform/ethyl acetate: 10/1 (volume/volume)), and the target product was collected and dried under vacuum. Thus, 0.56 g (yield: 82%) of purple 5,10,15,20-tetrakis($\alpha,\alpha,\alpha,\alpha$-o-(1-methylcyclohexylamido)phenyl)porphyrin was obtained.

Analysis results for this 5,10,15,20-tetrakis($\alpha,\alpha,\alpha,\alpha$-o-(1-methylcyclohexylamido)phenyl)porphyrin are shown in Table 1.

TABLE 1

Thin layer chromatography (chloroform/ethyl acetate: 10/1 (volume/volume): Rf: 0.50 (mono spot)). Infrared absorption spectrum ($cm^{-1}$): 1691 ($\nu C=O$(amide)), 3428 ($\nu NH$). Ultraviolet and visible absorption spectrum ($CHCl_3$, $\lambda_{max}$: 423, 516, 549, 590, 647 nm). FAB-MS spectrum (m/z): 1172 $[M]^+$. $^1H$-NMR spectrum ($CDCl_3$, TMS standard, $\delta$(ppm)): −2.6(s, 2H, innerH), 0.1(s, 12H, 1-methyl), 0.3–1.0(m, 40H, cyclohexyl), 7.5(t, 4H, phenyl-4), 7.6(s, 4H, amide-H), 7.8(t, 4H, phenyl-5), 7.9(d, 4H, phenyl-3), 8.8(d, 4H, phenyl-6), 8.9(s, 8H, pyrrole-$\beta$H).

Example 2

0.54 g (0.461 mmol) of the 5,10,15,20-tetrakis($\alpha,\alpha,\alpha,\alpha$-o-(1-methylcyclohexylamido)phenyl)porphyrin synthesized in Example 1 was dissolved in 10 ml of chloroform, and a methanol solution (2 ml) of 177 mg (1.15 mmol) of copper chloride dihydride and 233 mg (2.31 mmol) of triethylamine was added, which was then refluxed at 65° C. for 1 hour.

After confirming the insertion of copper ion into the porphyrin from the visible absorption spectrum of the reaction solution, the solvents were removed under reduced pressure and the residue was extracted with chloroform followed by washing with pure water several times. The chloroform layer was dried over sodium sulfate anhydride and subjected to filtration, followed by removal of solvents under reduced pressure. The residue was dissolved in a small amount of chloroform and subjected to fraction-purification by silica gel column (chloroform/ethyl acetate: 5/1 (volume/volume)). The target product was collected and dried under vacuum.

Thus, 0.45 g (yield: 79%) of purple 5,10,15,20-tetrakis($\alpha,\alpha,\alpha,\alpha$-o-(1-methylcyclohexylamido)phenyl)porphinatocopper(II) was obtained.

Analysis results for this 5,10,15,20-tetrakis($\alpha,\alpha,\alpha,\alpha$-o-(1-methylcyclohexylamido)phenyl)porphinatocopper(II) are shown in Table 2.

TABLE 2

Thin layer chromatography (chloroform/ethyl acetate: 10/1 (volume/volume): Rf: 0.74 (mono spot)). Infrared absorption spectrum (cm$^{-1}$): 1687 (vC=O(amide)), 3434 (vNH). Ultraviolet and visible absorption spectrum (CHCl$_3$, $\lambda_{max}$: 423, 541, 576 nm). FAB-MS spectrum (m/z): 1233 [M]$^+$.

Example 3

6.3 ml of distilled dimethylformamide, which was sufficiently deaerated using nitrogen, was cooled by ice-water, to which was added 7.4 mL of phosphorous oxychloride and stirred at ambient temperature for 1 hour to obtain a reddish orange Vilsmeier reagent. 14 mL of a dichloromethane solution of 0.45 g (0.36 mmol) of 5,10,15,20-tetrakis(α,α,α,α-o-(1-methylcyclohexylamido)phenyl)porphinatocopper (II) synthesized in Example 2 was added dropwise to the above reagent at ambient temperature. The color of the solution changed from purple to deep green with the progress of the reaction, enabling confirmation of the production of an iminium salt. The reaction mixture was refluxed for 18 hours, cooled and neutralized by adding 300 mL of an aqueous saturated sodium acetate solution, whereby the color of the reaction solution changed from green to purple.

Further, the stirring was continued at 40° C. for 3 hours and the resultant solution was extracted with chloroform, washed several times with pure water, dried using sodium sulfate anhydride and subjected to filtration, followed by removal of solvents under reduced pressure. The target product was collected by fraction-purification using silica gel column (chloroform/ethyl acetate: 5/1 (volume/volume)), then dried under vacuum. Thus, 0.22 g (yield: 50%) of purple 2-formyl-5,10,15,20-tetrakis(α,α,α,α-o-(1-methylcyclohexylamido)phenyl)porphinatocopper(II) was obtained.

Analysis results for this 2-formyl-5,10,15,20-tetrakis(α,α,α,α-o-(1-methylcyclohexylamido)phenyl)porphinatocopper(II) are shown in Table 3.

TABLE 3

Thin layer chromatography (chloroform/ethyl acetate: 5/1 (volume/volume): Rf: 0.53 (mono spot)). Infrared absorption spectrum (cm$^{-1}$): 1672 (vC=O(formyl)), 1692 (vC=O(amide)), 3428(vNH). Ultraviolet and visible absorption spectrum (CHCl$_3$, $\lambda_{max}$: 430, 552, 593 nm). FAB-MS spectrum (m/z): 1261 [M]$^+$.

Example 4

0.22 g (0.175 mmol) of 2-formyl-5,10,15,20-tetrakis(α,α,α,α-o-aminophenyl)porphinatocopper(II) synthesized in Example 3 was dissolved in 8 mL of dichloromethane and 2 mL of concentrated sulfuric acid was added to the mixture. The mixture was vigorously stirred at ambient temperature for 10 minutes whereby the color of the solution changed to green. This solution was added dropwise into a two-layer solution of chloroform and ice-water, which was then neutralized by adding sodium carbonate, whereby the color of the chloroform layer returned to purple. The chloroform layer was washed several times with pure water, then dried using sodium sulfate anhydride and subjected to filtration, followed by removal of solvents under reduced pressure. The residue was dissolved in a small amount of chloroform and subjected to fraction-purification by silica gel column (chloroform/ethyl acetate: 5/2 (volume/volume)). The target product was collected and dried under vacuum.

Thus, 0.18 g (yield: 84%) of purple 2-formyl-5,10,15,20-tetrakis(α,α,α,α-o-(1-methylcyclohexylamido)phenyl)porphyrin was obtained.

Analysis results of the resulting 2-formyl-5,10,15,20-tetrakis(α,α,α,α-o-(1-methylcyclohexylamido)phenyl)porphyrin are shown in Table 4.

TABLE 4

Thin layer chromatography (chloroform/ethyl acetate: 5/2 (volume/volume): Rf: 0.60 (mono spot)). Infrared absorption spectrum (cm$^{-1}$): 1672 (vC=O(formyl)), 1691 (vC=O (amide), 3429 (vNH). Ultraviolet and visible absorption spectrum (CHCl$_3$, $\lambda_{max}$: 432, 527, 555, 597, 662 nm). FAB-MS spectrum (m/z): 1200 [M]$^+$. $^1$H-NMR spectrum (CDCl$_3$, TMS standard, δ(ppm)): −2.3(s, 2H, innerH), 0.1–0.2(d, 12H, 1-methyl), 0.3–1.0(m, 40H, cyclohexyl), 7.4–7.6(m, 8H, amide-H, phenyl-4), 7.8–7.9 (m, 8H, phenyl-3,5), 8.7–8.9(m, 10H, pyrrole-βH, phenyl-6), 9.4(s, 1H, pyrrole-H), 9.6(s, 1H, formyl)

Example 5

177 mg (0.147 mmol) of 2-formyl-5,10,15,20-tetrakis(α,α,α,α-o-(1-methylcyclohexylamido)phenyl)porphyrin synthesized in Example 4 was dissolved in 2.5 mL of dichloromethane and 7 mL of methanol was added to the mixture, followed by sufficient deaeration using nitrogen. 53.6 mg (1.47 mmol) of sodium borohydride was added to the mixture under ice-cooling and stirred for 10 minutes, after which water was added to quench the reaction. The reaction solution was extracted with chloroform. The extract was washed with pure water several times, dried using sodium sulfate anhydride and subjected to filtration, followed by removal of solvents under reduced pressure. The residue was dissolved in a small amount of chloroform and subjected to fraction-purification by silica gel column (chloroform/methanol: 30/1 (volume/volume)). The target product was collected and dried under vacuum. Thus, 89.3 mg (yield: 50%) of purple 2-hydroxymethyl-5,10,15,20-tetrakis(α,α,α,α-o-(1-methylcyclohexylamido)phenyl)porphyrin was obtained.

Analysis results for the resulting 2-hydroxymethyl-5,10,15,20-tetrakis(α,α,α,α-o-(1-methylcyclohexylamido)phenyl)porphyrin are as shown in Table 5.

TABLE 5

Thin layer chromatography (chloroform/methanol: 30/1 (volume/volume): Rf: 0.29 (mono spot)). Infrared absorption spectrum (cm$^{-1}$): 1690 (vC=O(amide)), 3427 (vNH). Ultraviolet and visible absorption spectrum (CHCl$_3$, $\lambda_{max}$: 423, 517, 548, 591, 645 nm). FAB-MS spectrum (m/z): 1202 [M]$^+$. $^1$H-NMR spectrum (CDCl$_3$, TMS standard, δ(ppm)): −2.6(s, 2H, innerH), 0.1(m, 12H, 1-methyl), 0.3–1.0(m, 40H, cyclohexyl), 4.9(q, 2H, —CH$_2$OH), 7.4–7.6(m, 8H, amide-H, phenyl-4), 7.7–7.8 (m, 8H, phenyl-3,5), 8.6–8.8(m, 10H, pyrrole-βH, phenyl-6), 9.0(s, 1H, pyrrole-H).

Example 6

0.14 mL (1.15 mmol) of triethylamine was added to a dry dimethylformamide (2 mL) solution of 74.0 mg (0.287 mmol) 8-(2-methyl-1-imidazolyl)octanic acid-hydrochloride, whereby white hydrochloride precipitates were immediately observed. After stirring for 10 minutes, excess triethylamine was removed under reduced pressure using a vacuum pump. 2-Hydroxymethyl-5,10,15,20-tetrakis($\alpha,\alpha,\alpha,\alpha$-o-(1-methylcyclohexylamido)phenyl)porphyrin (35 mg, 28.7 μmol) synthesized in Example 5, 3.5 mg (0.0287 mmol) of 4-dimethylaminopyridine and 100.7 mg (0.488 mmol) of dicyclohexylcarbodiimide were added to the mixture, followed by stirring at ambient temperature under a light-shielded condition for 4 days, to obtain white salt of DCUrea precipitate. After removal of solvents under reduced pressure, the residue was dissolved in a small amount of chloroform and reprecipitated from benzene to purify the product. The precipitate obtained by filtration was dissolved in a small amount of chloroform and subjected to fraction-purification by silica gel column (chloroform/methanol: 10/1 (volume/volume)) to collect the target product, which was then dried under vacuum. Thus, 31.9 mg (yield: 76%) of purple 2-8-(2-methyl-1-imidazolyl)octanoyloxymethyl-5,10,15,20-tetrakis($\alpha,\alpha,\alpha,\alpha$-o-(1-methylcyclohexylamido)phenyl)porphyrin was obtained.

Analysis results for this 2-8-(2-methyl-1-imidazolyl)octanoyloxymethyl-5,10,15,20-tetrakis($\alpha,\alpha,\alpha,\alpha$-o-(1-methylcyclohexylamido)phenyl)porphyrin are shown in Table 6.

TABLE 6

Thin layer chromatography (chloroform/methanol: 10/1 (volume/volume): Rf: 0.60 (mono spot)). Infrared absorption spectrum (cm$^{-1}$): 1734 (vC=O(ester)), 1685 (vC=O(amide)), 3427 (vNH). Ultraviolet and visible absorption spectrum (CHCl$_3$, $\lambda_{max}$: 423, 517, 547, 591, 645 nm). FAB-MS spectrum (m/z): 1408 [M]$^+$. $^1$H-NMR spectrum (CDCl$_3$, TMS standard, δ(ppm)): −2.6(s, 2H, innerH), 0.1(m, 12H, 1-methyl), 0.3–1.2(m, 40H, cyclohexyl), 1.3–1.4(m, 10H, —CH$_2$)$_5$—), 1.6(m, 2H, —OC(=O)CH$_2$—), 2.4(s, 3H, 2-MeIm), 3.8(t, 2H, —CH$_2$Im), 5.3(s, 2H, Por-CH$_2$OC(=O)—), 6.8, 6.9(s, 2H, imidazole), 7.4–7.5(m, 8H, amide, phenyl-4), 7.6–7.8 (m, 8H, phenyl-3,5), 8.7–8.8(m, 11H, phenyl-6, pyrrole β-H).

Example 7

The reaction for introducing iron into porphyrin was carried out using conventional methods described in D. Dolphin (editor), The Porphyrin, (1978), Academic Press.

A three-neck flask was charged with an aqueous hydrobromic acid solution (1.62 mL), which was then completely deoxygenated by 30 minutes of nitrogen flow. 107.8 mg (1.93 mmol) of electrolytic iron was quickly added, the temperature raised to 80° C. and the mixture was stirred for 1 hour. When electrolytic iron was dissolved to form a transparent pale green solution, the temperature was raised to 130° C. to remove hydrobromic acid and water by evaporation.

A dry-tetrahydrofuran solution (5 mL) of 23.5 mg (16.1 μmol) of the 2-8-(2-methyl-1-imidazolyl)octanoyloxymethyl-5,10,15,20-tetrakis($\alpha,\alpha,\alpha,\alpha$-o-(1-methyl cyclohexylamido)phenyl)porphyrin synthesized in Example 6 and 21.3 mL (0.193 mmol) of 2,6-lutidine was added dropwise to the resulting pale white solid FeBr$_2$ in a nitrogen atmosphere and the mixture was refluxed for 12 hours. After the reaction was completed, solvents were removed under reduced pressure. The residue was extracted with chloroform, washed with pure water several times, dried over sodium sulfate anhydride and filtrated, followed by removal of solvents under reduced pressure. The residue was dissolved in a small amount of chloroform and subjected to fraction-purification (chloroform/methanol: 10/1 (v/v)) to obtain 17.6 mg (74%) of 2-8-(2-methyl-1-imidazolyl)octanoyloxymethyl-5,10,15, 20-tetrakis($\alpha,\alpha,\alpha,\alpha$-o-(1-methylcyclohexylamido)phenyl) porphinatoiron(III) complex-bromide.

Analysis results for the resulting 2-8-(2-methyl-1-imidazolyl)octanoyloxymethyl-5,10,15,20-tetrakis($\alpha,\alpha,\alpha,\alpha$-o-(1-methylcyclohexylamido)phenyl)porphinatoiron(III) complex-bromide are shown in Table 7.

TABLE 7

Thin layer chromatography (chloroform/methanol: 10/1 (volume/volume): Rf: 0.34 (mono spot)). Infrared absorption spectrum (cm$^{-1}$): 1740 (vC=O(ester)), 1685 (vC=O(amide)). Ultraviolet and visible absorption spectrum (CHCl$_3$, $\lambda_{max}$: 420, 504, 580, 648, 682 nm). FAB-MS spectrum (m/z): 1462 [M-Br]$^+$.

Example 8

2-8-(1-imidazolyl)octanoyloxymethyl-5,10,15,20-tetrakis($\alpha,\alpha,\alpha,\alpha$-o-(1-methylcyclopentylamido)phenyl)porphinatoiron(III) complex-bromide was quantitatively synthesized according to the same methods as described in Examples 1 to 7, except that 1-methylcyclopentanoic acid chloride was used in place of 1-methylcyclohexanoic acid chloride in Example 1 and 8-(1-imidazolyl)octanoic acid-hydrogen chloride was used in place of 8-(2-methyl-1-imidazolyl)octanoic acid-hydrogen chloride in Example 6.

Analysis results for the resulting 2-8-(1-imidazolyl)octanoyloxymethyl-5,10,15,20-tetrakis($\alpha,\alpha,\alpha,\alpha$-o-(1-methylcyclopentylamido)phenyl)porphinatoiron(III) complex-bromide are shown in Table 8.

TABLE 8

Thin layer chromatography (chloroform/methanol: 10/1 (volume/volume): Rf: 0.42 (mono spot)). Infrared absorption spectrum (cm$^{-1}$): 1740 (vC=O(ester)), 1685 (vC=O(amide)). Ultraviolet and visible absorption spectrum (CHCl$_3$, $\lambda_{max}$: 421, 503, 579, 648, 680 nm). FAB-MS spectrum (m/z): 1392 [M-Br]$^+$.

Example 9

2-8-(2-methyl-1-imidazolyl)undecanoyloxymethyl-5,10, 15,20-tetrakis($\alpha,\alpha,\alpha,\alpha$-o-(1-adamantaneamido)phenyl)porphinatoiron(III) complex-bromide was quantitatively synthesized according to the same methods described in Examples 1 to 7, except that 1-adamantanoic acid chloride was used in place of 1-methylcyclohexanoic acid chloride in Example 1 and 8-(2-methyl-1-imidazolyl)undecanoic acid-hydrochloride was used in place of 8-(2-methyl-1-imidazolyl)octanoic acid-hydrochloride in Example 6.

Analysis results for the resulting 2-8-(2-methyl-1-imidazolyl)undecanoyloxymethyl-5,10,15,20-tetrakis($\alpha,\alpha,\alpha,\alpha$-o-(1-adamantaneamido)phenyl)porphinatoiron(III) complex-bromide are shown in Table 9.

TABLE 9

Thin layer chromatography (chloroform/methanol: 10/1 (volume/volume): Rf: 0.25 (mono spot)). Infrared absorption spectrum (cm$^{-1}$): 1739 (vC=O(ester)), 1687 (vC=O(amide)). Ultraviolet and visible absorption spectrum (CHCl$_3$, $\lambda_{max}$: 420, 504, 578, 648, 680 nm). FAB-MS spectrum (m/z): 1646 [M-Br]$^+$.

Example 10

2-8-(2-methyl-1-imidazolyl)octanoyloxymethyl-5,10,15,20-tetrakis(α,α,α,α-o-(1-methylamidonorbornaneamido)phenyl)porphyrincobalt(II) complex was quantitatively synthesized according to the methods described in Examples 1 to 7, except that 1-methylamidonorbornic acid chloride was used in place of 1-methylcyclohexanoic acid chloride in Example 1 and cobalt was introduced into the center of porphyrin by reacting with cobalt chloride in dry tetrahydrofuran containing 2,6-lutidine in the method of Example 7.

Analysis results for the 2-8-(2-methyl-1-imidazolyl)octanoyloxymethyl-5,10,15,20-tetrakis(α,α,α,α-o-(1-methylamidonorbornaneamido)phenyl)porphyrincobalt(II) complex obtained are shown in Table 10.

TABLE 10

Thin layer chromatography (chloroform/methanol: 10/1 (volume/volume): Rf: 0.35 (mono spot)). Infrared absorption spectrum (cm$^{-1}$): 1742 (vC=O(ester)), 1688 (vC=O(amide)). Ultraviolet and visible absorption spectrum (CHCl$_3$, $\lambda_{max}$: 403, 521, 553 nm). FAB-MS spectrum (m/z): 1745 [M]$^+$.

Example 11

46.2 μg (0.03 μmol) of 2-8-(2-methyl-1-imidazolyl)octanoyloxymethyl-5,10,15,20-tetrakis(α,α,α,α-o-(1-methylcyclohexylamido)phenyl)porphinatoiron(III) complex-bromide synthesized in Example 7 was prepare into 10 ml of toluene anhydride solution and the atmosphere in the system was replaced with nitrogen. Then, the solution was mixed and stirred for 2 hours with an aqueous dithionous acid solution in a heterogeneous system to reduce the iron to the iron(II) state. Under nitrogen atmosphere, the toluene layer was extracted, dried over sodium sulfate anhydride and filtrated. The resulting toluene solution was transferred to and sealed in a measuring cell. Thus, a toluene solution of 2-8-(2-methyl-1-imidazolyl)octanoyloxymethyl-5,10,15,20-tetrakis(α,α,α,α-o-(1-methylcyclohexylamido)phenyl)porphinatoiron(II) complex was obtained. The visible absorption spectrum of this solution was $\lambda_{max}$: 441, 539, 558 nm, and corresponded to that of a five-coordinated deoxy-type complex in which one imidazole was coordinated.

When oxygen gas was blown into this solution, the spectrum immediately changed to $\lambda_{max}$: 424, 552 nm. This result indicated the formation of an oxygenated complex.

The visible absorption spectrum changed reversibly from the oxygenated type spectrum to the deoxy type spectrum by blowing nitrogen gas into this oxygenated complex solution for 1 minute, thus confirming that the adsorption-desorption of oxygen occurred reversibly.

Consequently, the adsorption-desorption of oxygen could be continuously carried out by repeating the operation of blowing oxygen and then nitrogen. The oxygen affinity (partial pressure of oxygen when 50% of the entire porphinatoiron is oxygenated (=P$_{1/2}$)), which serves as an index for the degree of affinity to oxygen was 20 torr (25° C.). Further, this oxygen coordinated complex oxidized and deteriorated gradually by a trace amount of water contained in toluene, and the half-life of this complex was determined to be 24 to 48 hours (25° C.).

Example 12

46.2 μg (0.03 μmol) of 2-8-(2-methyl-1-imidazolyl)octanoyloxymethyl-5,10,15,20-tetrakis(α,α,α,α-o-(1-methylcyclohexylamido)phenyl)porphinatoiron(III) complex-bromide synthesized in Example 7 and 2.2 mg (3.0 μmol) of dipalmitoyl phosphatidyl choline were mixed in methanol to prepare 15 μL of a methanol solution and the atmosphere in the system was replaced with nitrogen. Then, carbon monoxide was blown into the solution and an aqueous ascorbic acid solution was added to reduce the complex and to obtain a carbon monoxide complex. The resulting complex was poured into 3 mL of water (70° C.) to obtain a vesicle dispersion of carbon monoxide complex ($\lambda_{max}$: 427, 543 nm). Further, CO was dissociated by irradiation with light in a nitrogen atmosphere, whereby the visible absorption spectrum shifted to $\lambda_{max}$: 441, 547, 565 nm, indicating that the complex was converted into a five-coordinated deoxy-type with one imidazole was coordinated to it.

The formation of uniform bilayer membrane vesicles having a particle diameter of 100 to 200 nm was confirmed through observation of this solution by an electron microscope.

When oxygen gas was blown into this solution, the spectrum immediately changed to $\lambda_{max}$: 426, 554 nm, clearly indicating the formation of an oxygenated complex. The visible absorption spectrum changed reversibly from the oxygenated-type spectrum to the deoxy-type spectrum by blowing nitrogen gas into this oxygenated complex solution for 1 minute, thus confirming the reversible adsorption-desorption of oxygen.

In addition, it was confirmed that the adsorption-desorption of oxygen could be continuously carried out by repeating the operation of blowing oxygen and then nitrogen.

Example 13

3 mL of an aqueous phosphoric acid buffer solution (pH 7.4, 1/30 mM) of an albumine-heme complex (porphyrin/albumine: 8 (mol/mol)) prepared by incorporating 2-8-(2-methyl-1-imidazolyl)octanoyloxymethyl-5,10,15,20-tetrakis(α,α,α,α-o-(1-methylcyclohexylamido)phenyl)porphinatoiron(III) complex-bromide (20 μM) synthesized according to Example 7 into human serum albumine (2.5 μM) by the method described in JP-A No. 8-301873, was transferred to a quartz spectrometry cell and sealed under nitrogen. The visible absorption spectrum was $\lambda_{max}$: 445, 543, 567 nm, indicating that the porphinatoiron(II) complex incorporated formed a Fe(II) high-spin five-coordinated complex wherein one intermolecular axial base was coordinated.

When oxygen gas was blown into this dispersion solution, the $\lambda_{max}$ shifted to 428, 555 nm, clearly showing formation of an oxygenated complex. The visible absorption spectrum changed reversibly from the oxygenated type spectrum to the deoxy type spectrum by blowing nitrogen gas into this oxygenated complex solution for 1 minute, thus confirming the reversible adsorption-desorption of oxygen.

Furthermore, the adsorption-desorption of oxygen could be continuously carried out by repeating the operation of blowing oxygen and then nitrogen. The oxygen affinity (oxygen partial pressure when 50% of the entire porphinatoiron is oxygenated (=$P_{1/2}$)), which serves as an index for the degree of affinity to oxygen was 35 torr (37° C.). Also, this oxygen coordinating complex gradually oxidized and deteriorated and its half-life was determined to be about 9 to 24 hours (37° C.), which was outstandingly longer than formerly reported systems.

INDUSTRIAL APPLICABILITY

As described in detail above, a porphyrin metal complex, which is capable of forming a highly stable oxygen complex while maintaining an appropriate oxygen affinity is provided by the invention of the present application. This porphyrin metal complex can extend the stability of an oxygen complex while maintaining an oxygen affinity close to that of red blood cells. Furthermore, a novel oxygen infusion containing such a porphyrin metal complex acts as a highly stable preparation suitable for practical use. Further, the porphyrin metal complex of the present invention is applicable as a gas adsorbent, an oxygen-adsorption/desorption agent, a redox catalyst, an oxygenation reaction catalyst and the like, and is highly useful.

What is claimed is:

1. A porphyrin metal complex comprising:
a transition metal ion M of period 4 or 5 coordinating to a porphyrin derivative represented by the following general formula [I]

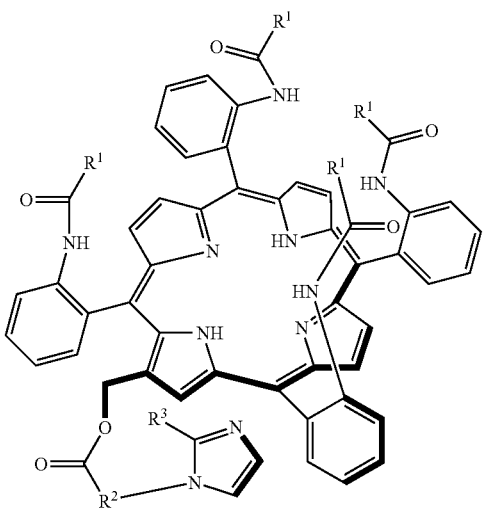

wherein $R^1$ is an alicyclic hydrocarbon group selected from the group consisting of a 1-substituted cyclopropyl group, a 1-substituted cyclopentyl group, a 1-substituted cyclohexyl group, a 1-methyl-2-cyclohexenyl group, a 1-substituted norbornyl group and a 1-substituted adamatyl group, $R^2$ is an alkylene group and $R^3$ is a group which does not hinder the coordination of an imidazolyl group to M.

2. A porphyrin metal complex represented by the following general formula [II]:

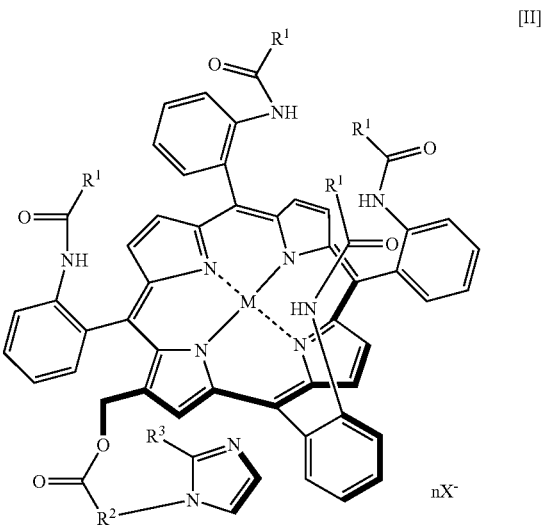

wherein M is a transition metal of period 4 or 5, $R^1$ is an alicyclic hydrocarbon group selected from the group consisting of a 1-substituted cyclopropyl group, a 1-substituted evelopentyl group, a 1-substituted cyclohexyl group, a 1-methyl-2-cyclohexenyl group, a 1-substiuted norbornyl group and a 1-substituted adamatyl group, $R^2$ is an alkylene group, $R^3$ is a group that does not hinder the coordination of the imidazolyl group to M, $X^{31}$ is a halogen ion and n denotes a number obtained by subtracting 2 from the valence number of M.

3. The porphyrin metal complex of claim 1, wherein $R^2$ is a $C_2$ to $C_{10}$ alkylene group.

4. The porphyrin metal complex of claim 1, wherein $R^3$ is a hydrogen atom or a substituent selected from the group consisting of a methyl group, an ethyl group and a propyl group.

5. The porphyrin metal complex of claim 1, wherein M is Fe or Co.

6. The porphyrin metal complex of claim 5, wherein M is Fe(II) or Fe(III).

7. The porphyrin metal complex of claim 5, wherein M is Co(II).

8. An oxygen infusion composition comprising at least two components, at least one of which is a porphyrin metal complex of claim 1.

9. An oxygen infusion composition prepared by incorporating and binding at least the porphyrin metal complex of claim 1 in a phospholipid vesicle, a fatty oil microsphere, albumin or an albumin multimer.

10. An oxygen infusion composition prepared by incorporating at least the porphyrin metal complex of claim 1 into human serum albumin, recombinant human serum albumin, human serum albumin dimer or recombinant human serum albumin dimer.

11. The porphyrin metal complex of claim 2, wherein $R^2$ is a $C_2$ to $C_{10}$ alkylene group.

12. The porphyrin metal complex of claim 2, wherein $R^3$ is a hydrogen atom or a substituent selected from the group consisting of a methyl group, an ethyl group and a propyl group.

13. The porphyrin metal complex of claim 3, wherein $R^3$ is a hydrogen atom or a substituent selected from the group consisting of a methyl group, an ethyl group and a propyl group.

14. The porphyrin metal complex of claim 2, wherein M is Fe or Co.

15. The porphyrin metal complex of claim 3, wherein M is Fe or Co.

16. The porphyrin metal complex of claim 4, wherein M is Fe or Co.

17. An oxygen infusion composition comprising at least two components, at least one of which is a porphyrin metal complex of claim 2.

18. An oxygen infusion composition comprising at least two components, at least one of which is a porphyrin metal complex of claim 3.

19. An oxygen infusion composition comprising at least two components, at least one of which is a porphyrin metal complex of claim 4.

20. An oxygen infusion composition comprising at least two components, at least one of which is a porphyrin metal complex of claim 5.

21. An oxygen infusion composition comprising at least two components, at least one of which is a porphyrin metal complex of claim 6.

22. An oxygen infusion composition comprising at least two components, at least one of which is a porphyrin metal complex of claim 7.

23. An oxygen infusion composition prepared by incorporating and binding at least the porphyrin metal complex of claim 2 in a phospholipid vesicle, a fatty oil microsphere, albumin or an albumin multimer.

24. An oxygen infusion composition prepared by incorporating and binding at least the porphyrin metal complex of claim 3 in a phospholipid vesicle, a fatty oil microsphere, albumin or an albumin multimer.

25. An oxygen infusion composition prepared by incorporating and binding at least the porphyrin metal complex of claim 4 in a phospholipid vesicle, a fatty oil microsphere, albumin or an albumin multimer.

26. An oxygen infusion composition prepared by incorporating and binding at least the porphyrin metal complex of claim 5 in a phospholipid vesicle, a fatty oil microsphere, albumin or an albumin multimer.

27. An oxygen infusion composition prepared by incorporating and binding at least the porphyrin metal complex of claim 6 in a phospholipid vesicle, a fatty oil microsphere, albumin or an albumin multimer.

28. An oxygen infusion composition prepared by incorporating and binding at least the porphyrin metal complex of claim 7 in a phospholipid vesicle, a fatty oil microsphere, albumin or an albumin multimer.

29. An oxygen infusion composition prepared by incorporating at least the porphyrin metal complex of claim 2 into human serum albumin, recombinant human serum albumin, human serum albumin dimer or recombinant human serum albumin dimer.

30. An oxygen infusion composition prepared by incorporating at least the porphyrin metal complex of claim 3 into human serum albumin, recombinant human serum albumin, human serum albumin dimer or recombinant human serum albumin dimer.

31. An oxygen infusion composition prepared by incorporating at least the porphyrin metal complex of claim 4 into human serum albumin, recombinant human serum albumin, human serum albumin dimer or recombinant human serum albumin dimer.

32. An oxygen infusion composition prepared by incorporating at least the porphyrin metal complex of claim 5 into human serum albumin, recombinant human serum albumin, human serum albumin dimer or recombinant human serum albumin dimer.

33. An oxygen infusion composition prepared by incorporating at least the porphyrin metal complex of claim 6 into human serum albumin, recombinant human serum albumin, human serum albumin dimer or recombinant human serum albumin dimer.

34. An oxygen infusion composition prepared by incorporating at least the porphyrin metal complex of claim 7 into human serum albumin, recombinant human serum albumin, human serum albumin dimer or recombinant human serum albumin dimer.

* * * * *